United States Patent [19]

Serfontein

[11] 4,153,685
[45] May 8, 1979

[54] BISMUTH COMPLEX PREPARATIONS

[75] Inventor: Willem J. Serfontein, Warmbad, South Africa

[73] Assignee: Schering Corporation, Kenilworth, N.J.

[21] Appl. No.: 362,282

[22] Filed: May 21, 1973

Related U.S. Application Data

[63] Continuation-in-part of Ser. No. 887,363, Dec. 22, 1969, abandoned, which is a continuation-in-part of Ser. No. 788,745, Jan. 3, 1969, abandoned.

[30] Foreign Application Priority Data

Nov. 23, 1968 [ZA] South Africa ................... 68/8411
Dec. 23, 1968 [ZA] South Africa ................... 68/8414

[51] Int. Cl.² ............... A61K 37/48; A61K 37/00; A61K 31/29
[52] U.S. Cl. .................................. 424/94; 424/177; 424/296
[58] Field of Search ................ 424/94, 131, 177, 296

[56] References Cited

U.S. PATENT DOCUMENTS 2,103,153  12/1937  Dunham ......................... 424/177
3,436,454  4/1969  Nouvel ............................ 424/10

FOREIGN PATENT DOCUMENTS 886170  1/1962  United Kingdom ................. 424/177

OTHER PUBLICATIONS

*The Extra Pharmacopoeia*, vol. 1, 24 ed. (1958), p. 294.

Primary Examiner—Frederick E. Waddell
Attorney, Agent, or Firm—Millen & White

[57] ABSTRACT

The invention relates to new pharmaceutical compositions comprising bismuth in the form of water-soluble proteinaceous complexes which are reversibly precipitable by alcohol, nondialysable and in which the bismuth is strongly bound. Preparations comprising the complexes are therapeutically useful for treating and prophylaxis against ulcers and inflammations, in particular of the gastro-intestinal tract. Altered soluble globular proteins, particularly enzymes are a preferred ligand. The preferred complexes are formed by the reaction of soluble proteinaceous material with a soluble source of bismuth in aqueous solution at up to 60° C. and pH 9-10. The formation of the complexes may be tested for by alcohol precipitation and/or gel filtration. These methods may also be used to concentrate the complexes.

25 Claims, No Drawings

BISMUTH COMPLEX PREPARATIONS

CROSS REFERENCES TO RELATED APPLICATIONS

This is a continuation-in-part of Ser. No. 887,363 filed Dec. 22, 1969 which in turn is a continuation-in-part of Ser. No. 788,745 filed Jan. 3, 1969, and the teachings of both of which by reference thereto are to be considered a part of the present disclosure. Both applications Ser. Nos. 887,363 and 788,745 are now abandoned.

BACKGROUND OF THE INVENTION

The present invention relates to complexes of proteinaceous material and bismuth used in pharmaceutical preparations useful against inflamed and ulcerated conditions. The complexes (subject to elementary precautions as to toxicity) lend themselves to internal use such as, in particular, by oral administration.

Pharmaceutical preparations intended for oral administration are known wherein a proteinaceous material and a bismuth salt is converted into a variety of compounds, sometimes of the nature of complexes. In most of these processes, the proteinaceous material is broken down drastically into fragments of very much lower molecular weight. In accordance with German Pat. No. 585163 protein is first subjected to fairly drastic digestion with strong alkali to achieve hydrolysis. The hydrolysed proteins are then converted into salts of various heavy metals (e.g. bismuth) and these bismuth salts are then further stabilised by reaction with tannic esters.

In accordance with German Pat. Nos. 588 710 and 655 684 the products are salts of metals such as bismuth and sulfhydrylceratic acid which is not a protein, but an acid formed by the hydrolysis of certain proteins.

German Pat. No. 666 467 relates to metal compounds (e.g. bismuth compounds) produced by coupling reaction between diazotised metal compounds and certain proteins. These products are not complexes at all.

German Pat. No. 101 683 again describes the manufacture of salts of bismuth and acidic degradation products of proteins.

German Pat. No. 202 955 relates to the manufacture of bismuth salts of paranucleic acid. Paranucleic acids are not proteins, but are hydrolysis products of considerably lower molecular weight than that of the proteins from which they are derived.

German Pat. No. 117 269 describes a comparatively drastic reaction which results in the formation of totally insoluble bismuth compounds.

French Pat. No. 577 407 again relates to the manufacture of bismuth salts of nucleic acids. Nucleic acids are not proteins, but are hydrolysis products of lower molecular weight, and the compounds formed are salts and not complexes.

None of the aforegoing preparations which are used i.a. for bacteriostatic purposes have ever been shown to have any efficacy for the treatment of ulcers, in particular gastro-intestinal ulcers. None of these preparations contain water-soluble non-dialysable bismuth protein complexes which are reversably precipitable by alcohol and in which the bismuth is stably bound and not removable by dialysis.

For the treatment of gastro-intestinal disorders, including ulcers, it has been suggested to use commercial bismuth preparations of the type generally referred to as bismuth ammonium citrate (BAC) or occasionally tartrate. BAC commercially available for that purpose is in reality mostly "bismuth ammonium citrate cum pepsin." The preparation thereof is described in various issues of BPC (British Pharmaceutical Codex), e.g. of 1929. Such compositions are also known in the pharmaceutical trade as "Mistura Pepsini et Bismuthi Compositum sine tinctura nucis vomicae et acid hydrocyanicum." Such compositions usually contain cochineal dye or carmine, which contains 50% of the anthraquinone type dye carminic acid, ($C_{12}H_{22}O_{13}$). The other constituents normally present in BAC solutions--notably glycerol or sugar-presumably serve to stabilize the solution. Such compositions were always believed to be mere mixtures of the starting materials. However, the present applicant has in fact discovered (non-published research work) that in the mixing of the ingredients of BAC with pepsin certain complexes (or addition compounds) of protein and bismuth are also formed. However, in those complexes the bismuth is only loosely bound and is removed immediately when subjected to dialysis. It has never been possible to prove for those prior art preparations any efficacy in gastric ulcer therapy statistically significantly better than Placebo.

Protein complexes of bismuth have been known in the literature in the context of using bismuth as a precipitant for proteins. The present invention by way of contrast relates to novel, essentially water-soluble proteinaceous complexes of bismuth.

The conventional treatment of ulcers of the intestinal tract, in particular gastric ulcers has been surgery and/or strict dieting, antacid treatment and rest.

It is an object of the invention to provide improvements in the context of treatment of and prophylaxis against inflammatory conditions and ulcers, in particular ulcers of the gastro-intestinal tract such as peptic and duodenal ulcers.

It is also an object to provide a treatment of gastric ulcers requiring little or no dieting and which is carried out without antacid treatments.

BRIEF DESCRIPTION OF THE INVENTION

In accordance with the present invention, there is provided a pharmaceutical preparation, comprising a therapeutically effective amount of a proteinaceous bismuth complex, which is essentially water-soluble, essentially reversibly precipitatable by alcohol, and in which the presence of bismuth in a form non-removable by dialysis is an essential characteristic.

More particularly there is provided a pharmaceutical preparation containing as an essential active ingredient an amount effective in anti-inflammatory and anti-ulcer therapy of a water-soluble complex of (a) Bismuth in its trivalent state of oxidation,
(b) a physiologically acceptable, water-soluble proteinaceous molecule, having an affinity for said bismuth,
(c) optional supplementary molecular entities selected from the group consisting of neutral molecules, and ions occupying available sites in the complex molecule, said complex being reversibly precipitable by alcohol and an essential characteristic being the presence in the complex of bismuth bound so strongly as to be stable against removal by dialysis, the complex as a whole being non-dialysable.

The stability of complexes is known to be dependent on favourable spacial inter-relationships of the complex forming constituents. Complex molecules consist of co-ordinating atoms or groups on the one hand, around which an appropriate number of other groups (known as ligands) are "packed" in space. The number of such ligands surrounding the co-ordinating atom or group is known as the so-called "co-ordination number." Bismuth is known to have a very pronounced tendency to become a "co-ordinating atom" in complexes, its co-ordination number being from 3 to 6, usually 4 to 6 in complexes according to the invention. The ligands of complexes are formed by atoms, groups or moieties, having "nucleophilic properties".

The present complexes can be visualised as comprising co-ordinating atoms represented by the said bismuth in its trivalent state of oxidation. These bismuth atoms are partly "wrapped up" by nucleophilic regions of appropriate proteinaceous molecules. In order to do so, the protein molecule must obviously satisfy certain spacial requirements, in order to make it physically possible for bismuth to be thus accommodated. In addition, there must be present nucleophilic (e.g. OH, SH, $NH_2$, COOH) moieties in the protein molecule which satisfy the spacial requirements and have the required affinity to enter into co-ordination with the bismuth. This will be readily understood by the skilled chemist. It will also be readily understood that because of the large size of protein molecules by comparison with bismuth atoms, a single protein molecule may thus accommodate in different regions of the molecule a plurality of bismuth atoms.

Also because of the size and shapes of the protein molecules it will obviously be difficult, if not impossible for protein alone to satisfy the most stable co-ordination number of bismuth in the particular type of complex. The purpose of the "supplementary entities" referred to further above is therefore firstly to provide additional nucleophilic ions, molecules or groups which act as additional ligands to occupy the remaining co-ordination sites so as to satisfy the co-ordination number of the bismuth atoms.

Thus (c) in the above definition in the preferred embodiments includes ammonia, and an organic acid capable of forming water soluble salts with bismuth. Particularly suitable because of their nucleophilic properties, are lower hydroxycarboxylic acids, in particular those having between 2 and 6 carbon atoms, including di- and poly-carboxylic acids and including di- and poly-hydroxy acids.

In accordance with the above definition, (c) also includes neutral molecules selected from the group consisting of physiologically acceptable dyes, sugars, glycols and glycerols, all having nucleophilic properties, rendering them capable to enter into co-ordination as ligands with bismuth. These groups and molecules thus stabilise the complex without having to play any part in the actual efficacy of the preparation. It is preferred however, to incorporate in the complex a small percentage of suitable dyes, such as dyes of the anthraquinone type, e.g. cochineal or carmine or azo-rubrium. These dyes impart a pleasant colour to the complex and thereby also to the preparation as a whole.

Examples of suitable hydroxycarboxylic acids for incorporation in the complexes are lower alpha, beta, gamma and delta hydroxy-derivatives of fatty acids, dibasic and tribasic acids, for example citric acid, malic acid, tartaric acid, lactic acid. In the case of optically active acids, all complex forming optically active forms as well as racemates are included.

The above complexing agents (ligands) need not all be confined to the "inner sphere" of the bismuth complex (i.e. molecules and groups which are packed directly around the bismuth atom, but some may also participate in the "outer sphere" in which water of outer sphere hydration may also be present.

Referring now more specifically to the proteinaceous constituent of the complex it will be understood that whilst the proteinaceous constituent must participate in the formation of the inner sphere (to account for the strong bond between the bismuth and the macromolecular part of the complex) it can in addition also participate in the formation of any "outer sphere."

It was found that there exists a correlation between water-solubility of the complex, and therapeutic efficacy, the more highly water-soluble complexes producing preparations having the greater efficacy. Generally speaking there also exists a correlation between water solubility of the protein constituent and of the complex as a whole.

Accordingly, insoluble fibrous proteins such as collagens, e.g. gelatine, elastins and keratins, are not preferred as such, although they may be rendered more suitable for the purposes of the invention if they are first rendered soluble by various known chemical means, without drastically breaking down their molecular size.

The desirability of conjugated proteins for the purposes of the invention, is again a matter of water solubility. Thus casein is a conjugated protein (although it is also a globulin, belonging to the group of globular proteins). It is sparingly soluble, and its complexes made in accordance with the invention, result in preparations which appear to have a lower efficacy in anti-inflammatory and anti-ulcer therapy than the more preferred complexes in accordance with the invention. Certain albumins are representatives of the class of conjugated proteins as well as being globular proteins. Being readily soluble in water they also form complexes in accordance with the invention which are readily soluble and generally have an anti-ulcer and anti-inflammatory efficacy superior to that of casein complexes.

The protamines (salmine, clupeine, sturine) are capable of forming soluble complexes. These protamines (although also globular) are of comparatively low molecular weight. At present, the proteins of higher molecular weight are more preferred for the purposes of the invention.

The preferred proteins for the purposes of the present invention are generally the readily water-soluble globular proteins, and in particular, the enzymes, e.g. pepsin, papain, trypsin or chymotrypsin, to mention but a few. Pepsin is particularly preferred.

As a general rule, the proteins (and this goes particularly for the water-soluble globular proteins) are not employed in their unaltered condition in which they occur naturally, but in the form of an alteration product formed when the protein is subjected to mild denaturation and chemical degradation sufficiently so (in the case of globular proteins) to open up the globular structure of the globular protein, and to produce the required affinity for bismuth whilst essentially preserving the non-dialysable molecular size of the protein.

Amongst the globular proteins that may be used in this matter are various tissue proteins, in particular the enzymes, oxygen carrying proteins, protein hormones, albumins (egg albumin, different types of serum albumins), globulins and histones.

In the preferred compositions, the complex is an addition product of said alteration product of the protein, and a water soluble double salt of bismuth, more particularly an addition product of said alteration product, and a water-soluble physiologically compatible bismuth ammonium salt of an organic hydroxyacid.

Certain preferred preparations are in the form of an aqueous solution, more particularly an aqueous syrup, wherein at least 3 mg/ml of the said bismuth is bound in a manner stable against removal by dialysis, the complex being an addition product of a substance selected from the group consisting of bismuth ammonium citrate, bismuth ammonium tartrate, bismuth ammonium lactate, and bismuth ammonium malates, or quite generally of a water-soluble bismuth salt of a lower hydroxy carboxylic acid.

It was also determined empirically that satisfactory anti-ulcer and anti-inflammatory efficacy is obtained when the preparation is in the form of an aqueous solution containing at least 27 mg. bismuth per milliliter of said solution, such bismuth being derived from a water-soluble bismuth ammonium salt of an organic hydroxyacid, at least 10% of said bismuth being stable against removal by dialysis.

A successful preparation of this type is a conversion product of a starting material having essentially a composition similar to bismuth ammonium citrate cum pepsin (Commercial name: Mistura Pepsini et Bismuthi Compositum sine tinctura nucis vomicae et acid hydrocyanicum) substantially according to British Pharmaceutical Codex wherein at least 27 mg/ml soluble Bi are present derived from said bismuth ammonium citrate or its equivalent, a substantial proportion of the bismuth being present in the form of soluble proteinaceous complexes which on addition of a suitable amount of alcohol are readily precipitable in the form of a thick gelatinous precipitate which rapidly sinks to the bottom, and which preparation, when subjected to gel filtration at pH 9.0 on a saturated column of crosslinked polydextran of a grade suitable for the separation of peptides and globular proteins in the molecular weight range of about 4,000 to 150,000 yields two peaks of which the first peak represents in excess of 10% of said bismuth. Complexes of the type to which the present invention relates are concentrated in that peak.

Preferably the said first peak represents between 20 and 80% of said bismuth and preferably in excess of 29 mg/ml of said soluble bismuth are present. For example, where the preparation is in the form of a syrup the said bismuth concentration is advantageously between 30 and 40 mg/ml. However, the preparation may be brought into even more concentrated active form, including solid form, e.g. powder form, either for administration in such form, either for administration in such form, e.g. after incorporation in capsules or tablets, e.g. sugar-coated tablets, or for purposes of storage or transport and subsequent redissolving.

Also, in accordance with the invention, there is provided a process for the manufacture of a pharmaceutical preparation having anti-inflammatory and anti-ulcer efficacy, which comprises:

reacting a double salt of bismuth in its trivalent state of oxidation with a physiologically acceptable water-soluble proteinaceous substance, the molecules of which have an affinity for said bismuth to form a water-soluble proteinaceous bismuth complex, which is reversibly precipitable by alcohol, at least a substantial part of the bismuth being bound so strongly as to be stable against removal by dialysis, the complex as a whole being non-dialysable, and incorporating said complex in an effective concentration in a galenic form adapted for carrying the complex into the region to be treated.

The said reacting is advantageously carried out in aqueous solution.

The preferred process comprises subjecting a water-soluble globular protein to mild chemical attack, to achieve partial degradation and denaturation sufficiently so to open up the globular structure of the globular protein, and to produce said affinity whilst essentially preserving the non-dialysable molecular size of the protein, and then converting the protein thus altered into said complex. The said mild chemical attack preferably takes place in a moderately alkaline, more particularly ammoniacal aqueous solution at modestly raised temperature conditions, more particularly not exceeding 65° C., preferably not exceeding 60° C. Preferably the aqueous alkaline medium has a pH between 9 and 10.

The preferred process is carried out in the presence of an organic hydroxyacid as described further above, which is then incorporated into the said complex.

More particularly, the aforesaid double salt of bismuth is present in the aqueous medium, and the process is carried out in the presence of ammonium ion.

In accordance with a preferred embodiment, the complex is brought into syrup form, containing at least 3 mg./ml of bismuth bound in the said form, which is stable against removal by dialysis. This may include a step of concentrating the complex to the desired concentration.

In accordance with a particularly preferred embodiment of the invention, there is used as starting material bismuth ammonium citrate with pepsin, of the type "Mistura Pepsini et Bismuthi Compositum sine tinctura nucis vomicae et acid hydrocyanicum" and wherein the pepsin may be replaced, completely or in part, by a proteinaceous compound having the analogous reactivity towards bismuth, and the reaction between the double salt of bismuth and the proteinaceous substance is continued until at least 10%, preferably at least 20% of the bismuth derived from the starting material has formed the water-soluble, by alcohol reversibly precipitable bismuth-protein complexes.

The degree of conversion may be monitored by precipitation and/or gel filtration of the complexes.

The process may comprise the step of concentrating the complexes by precipitation of the complexes with a suitable precipitant for proteins, for example an "active" aqueous solution is subjected to precipitation of a concentrated "active" fraction with a water-soluble organic solvent such as alcohol or acetone.

Other precipitation techniques normally used for the precipitation of macro molecules—especially proteins—such as using salts (ammonium sulphate) or polyethyleneglycol, could also be employed for this purpose.

Alcohol is considered particularly convenient. When in excess of about 2 volumes, say between 3 and 5 volumes thereof are added to BAC solution containing pepsin and carmine dye and after having been subjected to the chemical conversion described further above there results a thick, gelatinous reddish precipitate which rapidly sinks to the bottom of the container. The supernatant fluid may then be easily decanted, the precipitate dissolved in water to yield a cherry red solution, very similar to the original from which a coloured precipitate which does not stick to the glass walls of the container may again be obtained. After repeated precipitations of this nature, the material can be dried (by exposure to the air or in a vacuum dessicator) to yield a pinkish bismuth containing solid substance. This substance may be redissolved in water to yield a cherry red solution similar to the original solution in many respects. The preparation and pharmaceutical applications of crystalline, semi-crystalline or amorphous products in this manner from BAC solutions, are considered to be included in the present application.

The attainment of good yields of the said complexes is facilitated by employing a starting material for the reaction wherein the protein concentration based on soluble bismuth is higher than that of ordinary commercial bismuth ammonium citrate with pepsin when prepared according to the British Pharmaceutical Codex, more particularly in the ratio of protein to bismuth being in excess of 1 to 4, preferably at least 1 to 3.

In addition it is advantageous to increase the concentration of citrate or its equivalent.

Alternatively, or in addition the process may also comprise the step of concentrating the complexes by evaporation of water under conditions at which the complexes are substantially stable.

Alternatively or in addition, the process may comprise the step of concentrating the complexes by gelfiltration.

The complexes described in the aforegoing in the context of the pharmaceutical preparation, and the process for making such preparations are novel compounds, and have not been previously described in the literature.

Also in accordance with the invention, there is provided a method of treating a patient suffering from ulceration which comprises introducing to the region of ulceration a pharmaceutical preparation as described above in amounts effective to heal said ulceration. The method is applied particularly to the healing of gastrointestinal, particularly peptic ulceration, in which case pharmaceutical preparations as defined above, are administered orally. In contrast to conventional methods of treating peptic ulcers, the diet of the patient is adapted on purpose to favour gastric acidity, antacids, and foods (such as milk and milk products), which tend to raise the pH being avoided. In fact, in the event of patients with pronounced gastric hypoacidity (pH higher than 4.0), it is advisable to administer dilute hydrochloric acid immediately before taking the preparation in accordance with the invention. The deposition of bismuth on the ulcer site has been observed clinically.

Also, in accordance with the invention, there is provided a method of prophylactic therapy for patients treated with drugs, having a tendency to cause the formation of peptic ulcers, which comprises administering orally to such patient a pharmaceutical preparation as defined above, in an amount effective to combat said tendency. Examples of such drugs which have a tendency to cause the formation of ulcers are the salicylates, phenylbutazone, drugs employed in cortisone therapy, cholinergic agents, and generally substances which promote the liberation of histamine.

Whilst the invention can be applied particularly readily to the treatment of ulcers in the upper part of the gastro-intestinal tract, the administration of the preparation to ulcer or inflammation sites lower down, may be facilitated by including the preparation in capsules designed to dissolve after having passed through the stomach.

Clinical observations support the hypothesis that the therapeutic efficacy of the complexes is due in many cases to reactions in vivo Bismuth-protein+receptor→Bismuth-receptor+protein, wherein the receptor is a tissue site having affinity for bismuth.

In accordance with the above reaction, the protein constituent of the complex has no direct effect on efficacy (apart from its solubilising effect), which is in keeping with practical observations. The choice of protein as well as the process to which the protein is subjected will of course influence the isoelectric point of the complex, and this in turn may influence the ease with which the complex reacts with the ulcer tissue depending on the pH prevailing in the region of such tissue.

EXAMPLE 1

Method of preparation (using pepsin as the protein)

Starting Materials

The starting materials in the present example were either a commercial bismuth ammonium citrate with pepsin hereinafter referred to as BAC, containing added 0.1% cochineal dye or azo-rubrium. In other parts of the example the starting material was specially prepared as described. Various suitable BAC preparations are described in British Pharmaceutical Codex, e.g. in the editions of 1907 and 1934. In their manufacture bismuth citrate (or tartrate) is dissolved in aqueous ammonia and the pH is adjusted to 9.6. The pepsin (commercial preparations contain pepsin and bismuth in a ratio of up to approximately 1:4, for the present purposes a higher ratio is advantageous), are added as an aqueous solution. Some commercial preparations of this type in addition contain glycerine. Cochineal, or azo-rubrium, is added in amounts of about 0.1%.

Procedure A

Syrup simplex is added to 60 liter commercial aqueous BAC solution (ratio pepsin to bismuth 1:4) to raise the sugar concentration of the solution to 3%. 900 g potassium citrate are dissolved in that solution, and the solution is diluted to 75 liters with water. The pH of the solution is adjusted to 9.6 with ammonium hydroxide.

The conversion in accordance with the invention is carried out as follows:

The temperature of the batch is raised slowly and very carefully to 60° C. in the course of at least 5 hours. Care is taken that a temperature of 65° C. is not exceeded. The temperature of 60° C. is maintained for a period of several hours until an adequate degree of conversion is determinable by the following "activity" test:

(i) Take a small sample of the solution and add 3 volumes of absolute alcohol. If appreciable "activity" has formed a characteristic red gelatinous precipitate will form immediately which readily sinks to the bottom and which can be redissolved in water. If the test is strongly positive, carry out the next test:

(ii) G 100 (a cross-linked polydextran of a grade suitable for the separation of peptides and globular proteins in the molecular weight range 4 000–150 000) in an appropriate quantity of 0.05 M Tris buffer pH 9.0 for a period of 72 hours and pack a column (dimensions approximately $35 \times 2\frac{1}{2}$ cm after packing) with the swollen gel. Apply 2 ml of "active" solution and develop column in the usual manner with 0.05 M Tris (flow rate 50 ml per hour) to saturate column. Repeat with another 2 ml portion of "active" solution until column is saturated and the pink band can be eluted and collected. Now apply exactly 1.0 ml of "active" solution and develop with Tris buffer pH 9.0 (flow rate 25-30 ml per hour) and collect first coloured band quantitatively. Make this fraction up to a convenient volume with distilled water and use an appropriate portion for a quantitative determination of bismuth.

The preparation is considered suitable for therapeutic purposes when a concentration level of 3.0 mgm bismuth (or more) per ml of preparation applied to the column was present in the total pink band. In practice values of about 5.0 mg Bi per ml or higher are usually attained.

Active preparations obtained in this manner contained 30–36 mgm of total Bismuth/ml. (Final pH 9.6–9.8), of which between 10 and 20% are bound in the form of the said complexes, and are not removed by dialysis. If required, the solution may be clarified by filtration.

Procedure B

This is carried out in a similar manner to procedure A by using ammonium citrate instead of potassium citrate and by using a potassium hydroxide solution (20%) to adjust the pH value of the solution.

Procedure C (For preparations containing an increased percentage of added protein - pepsin)

6030 g of bismuth citrate are dissolved with the aid of a mixture consisting of 430 ml concentrated (25%) ammonium hydroxide solution and 21.2 L of aq. dist. (The pH of the solution should be 9.6 at this stage).

2000 g of pepsin are dissolved in a minimum quantity of aq. dist. and the solution added to the bismuth solution.

Aq. chloroform BP 810 ml, liq. Azo-rubri BPC 2070 ml, potassium citrate 680 g and syrup simplex 21.6 L are then added and dissolved in the mixture and the volume finally adjusted to 78.0 L with aq. dist. 900 g. of potassium citrate are then dissolved in the solution, the final pH adjusted to 9.6 with $NH_4OH$ solution. The mixture is then converted as described in Procedure A.

Procedure D

The method in accordance with Procedure A is carried out, but using only 45 L of BAC solution. The final solution contains only about 20 to 26 mg/ml of Bi. and when the solution is converted under identical conditions as a typical batch of Procedure A it is found difficult to attain the empirical "activity" standard described.

The activity is boosted as follows:
(i) To half of the matured solution one adds 4 volumes of alcohol. A precipitate is formed which is added to the other half of the matured solution. or
(ii) Test (ii) in Procedure A is scaled up. A portion of the matured solution is chromatographed to isolate the pink band of which enough is added back to original matured solution to raise its total bismuth content to above 27 mg/ml.

Procedure E

One volume of BAC solution converted as described for Procedure A was mixed with 3–4 volumes of alcohol to yield a thick, gelatinous reddish precipitate, which rapidly sinks to the bottom of the container. The supernatant fluid is decanted, and the precipitate re-dissolved in water, yielding a cherry red solution very similar to the original "active" solution. By repeated precipitation with alcohol in this manner, a coloured precipitate is finally obtained, which does not stick to the glass walls of the container.

The material is collected by decantation and/or filtration, washed with 80% alcohol and dried by exposure to the air or in a vacuum dessicator to yield a pinkish, bismuth containing solid, which is readily reduced to a powder by grinding. The final powder obtained in this manner is used for the preparation of tablets or capsules containing 50 mg bismuth each, a single dose being represented by between 1 and 3 capsules or tablets.

Procedure F

Procedure A is modified by adding 500 g additional pepsin to the solution prior to the "activation" step (conversion). In this manner the ratio of pepsin to bismuth is raised to just exceeding 1:3. In this manner, it becomes possible to complete the conversion within 5 hours, and as a rule more than 20% of the bismuth enters into the complex in that period.

Clinical

The product (I) in accordance with Procedure D, prior to steps (i) or (ii) is compared with the product (II) from Procedure A.

| One ml contains | Analyses | |
| --- | --- | --- |
|  | I | II |
| Total bismuth | 20–26 mg | 30 to 34 mg |
| Bismuth in pink band | 2.7–3.0 mg | 4.5 to 5.5 mg |

Clinical results

The preparations were administered to peptic ulcer patients three times daily, 5 ml half an hour before each meal, agents aimed at increasing alkalinity being avoided. The periods of treatment were about 6 weeks. Complete healing or drastic size reduction of ulcers were considered indicative of successful treatment.

Preparation I

Over a prolonged period the success rate was about 50–60%.

Preparation II

Over a period of several months there was observed a definite improvement in the rate of healing as well as the percentage of successes which is now estimated at at least 70%. At one hospital 14 patients were treated who were all healed completely with so far no recurrence of symptoms.

The comparison of the results demonstrates the following:
(a) in both cases the success rates were considerably higher than with Placebo.
(b) preparation I marginally complies with the empirical "activity" test requirements in respect of the concentration of the pink brand. Preparation II demonstrates that after the concentration of the amount of converted bismuth in the preparation by several percent (which is facilitated by slightly increasing the total bismuth content), there is observed an immediate rising of the success rate.

Dialysis Test

The starting solution according to procedure C was compared with the same solution of the conversion by dialysis for 72 hours against distilled water. In the first case, the bismuth was leached out almost completely. In the case of the converted preparation, more than 25% of the original bismuth were retained. The formation of the complexes can also be demonstrated by comparing the electrophoresis (gelelectrophoresis or paperelectrophoresis of the starting solution, and the solution after the completed conversion reaction respectively. There is also a remarkable difference between the osmotic properties of the solution before and after conversion.

EXAMPLE 2

Example 1, procedure C is carried out using instead of the solution of Azo-rubri, 80 g of carmine dye dissolved in the minimum volume of chloroform-water.

The preparation is used as in Example 1.

EXAMPLE 3

The method according to Example 1, Procedure C is carried out using instead of pepsin one of the following proteins having an iso-electric point below 5:

Ovalbumin, Myoalbumin, gelatin, alpha-casein, alpha-ovomucoid, alpha-ovomucoid, thymonucleohistone.

EXAMPLE 4

A solution is prepared substantially in accordance with the procedure of Example 1, using instead of pepsin one of the following proteins having an iso-electric point in the alkaline region:

trypsin; chymotrypsin.

A concentrate of the proteinaceous bismuth complexes is prepared by adding to the solution four times the volume of alcohol to result in the precipitation of the complexes.

The precipitate is encapsulated in capsules containing 50 mg of bismuth each and being of a type which dissolves immediately after having passed through the stomach.

The capsules are to be administered three times daily, a single dose being between 1 and 3 capsules in the treatment of ulcers of the duodenum, jejunum and ileum.

EXAMPLE 5

Preparation of other Bismuth protein complexes

The method of Example 1 procedure C was followed with the following proteins: Pepsin, ovalbumin, bovine serum albumin, gelatin, casein, trypsin and papain, using the following quantities of ingredients in the starting material.

| | |
|---|---|
| Ammonia (25%) | 17 ml |
| Bismuth citrate | 35 g |
| Potassium citrate | 15 g |
| Protein | 7.5 g |
| Methyl parahydroxybenzoate | 6.0 g |
| | preservatives |
| n-propyl parahydroxybenzoate | 0.6 g |
| Amaranth sol. (BP) | 6.2 ml |
| Carmine sol. (BP) | 1,25 ml |
| 60% sucrose solution | 117 ml |

| -continued | |
|---|---|
| Final volume | 560 ml |

In all cases the final pH was adjusted to 8,5.

The conversion solutions had the following appearances: Clear solutions were formed with serum albumin, pepsin, ovalbumin and trypsin. Slight turbidity was observed with papain. Heavy turbidity was observed with casein. Gelatin formed a heavy insoluble precipitate, although the solution did retain in solution some complexes in accordance with the invention as well.

10 ml. of each of the filtered solutions were treated with 30 ml. ethylalcohol (96%).

With pepsin, a heavy flocculent precipitate was formed which settled to the bottom of the tube immediately. A fine whitish precipitate was formed with bovine serum albumin, and ovalbumin, which settled much more slowly (whitish red). With trypsin and papain the turbidity was heavier, and the (whitish red) precipitate settled more quickly (but more slowly than with pepsin).

With casein and gelatin a white milky turbidity was obtained, which in the case of casein settled as a heavy white precipitate after 24 hours. It had not settled out in the case of gelatin. All precipitates were soluble in water.

Electrophoresis

The Beckman microzone cellulose acetate membrane electrophoresis system was used to investigate the various preparations. Bismuth containing protein fractions (i.e. the complexes) were detected in all cases, although the conditions had to be modified in some cases. Suitable conditions for the separation of the complexes of pepsin, casein, and serum albumin were for example the following:

buffer: barbiturate buffer, ionic strength 0.075; pH 8.6
voltage: 250 V.
current: 4.5 to 9.5 mA
time: 20 minutes.
colouring agents: Ponceau-S for proteins and $H_2S$ for bismuth.

Some electrophoresis patterns have a characteristic pine-tree-like shape. The mobilities indicate that the iso-electric points of the complexes are different from those of the original proteins. Under the conditions of the experiment, all protein complexes migrated to the annode with the exception of the trypsin complex which moved slightly towards the cathode.

Anti-ulcer activity (in rats)

80 young adult rats (both sexes) were divided into 8 equal groups, one for each of the seven preparations and one serving as control. Ulceration was induced in all test animals (after starving for one day) with phenylbutazone, administered orally twice on the same day under light ether anaesthesia.

Before administration, the various test preparations were diluted with an equal volume of water. The dosage level was 1 ml. (undiluted) per animal every six hours (three times), the first dosage being given two hours after the last phenylbutazone treatment. The control group received one ml. of saline every six hours (three times) simultaneously with the experimental groups.

24 hours after the last treatment, all animals were sacrificed. The stomachs were removed, and each organ treated with formalin to reveal the ulcers as follows. The cardia was cut, and the duodenum closed in the pyloric region after the organ had been washed repeatedly with saline to clean out all of the gastric contents. The organ was then inflated from the cardia side by injecting approximately 15 ml of 10% formalin, and closed in the inflated condition. The inflated organs were then examined under strong light to reveal ulcerations, and the degree of ulceration was determined with the aid of an "ulcer index" which was determined as follows:

| ULCER INDEX. | |
|---|---|
| Assigned value | Lesions. |
| 0 | No lesion |
| 1-3 | haemorrhagic spots |
| 4-6 | small ulcers |
| 7-9 | large ulcers |
| 10 | perforation. |

The following were the ulcer indices (average) observed in the different groups:

| Group: | Treatment | Ulcer index | Number of animals |
|---|---|---|---|
| I | Pepsin | 2.4 | 10 |
| II | Ovalbumin | 5.1 | 10 |
| III | Bovine serum albumin | 4.1 | 10 |
| IV | Gelatin | 7.0 | 10 |
| V | Casein | 5.9 | 10 |
| VI | Trypsin | 2.9 | 10 |
| VII | Papain | 3.1 | 10 |
| VIII | Control | 8.2 | 10 |

THERAPEUTIC EFFICACY

The results with phenylbutazone induced gastric ulcers in rats must not be correlated with efficacy in humans in absolute terms. However, in lengthy clinical and laboratory tests with pepsin complexes in accordance with the invention (including double-blind cross-over-tests on humans it has already been established that this animal test system provides a reasonable degree of correlation superior to some other tests (e.g. cortisone induced ulcers).

Whilst it would be wrong to conclude from the aforegoing that the trypsin complex is less active than the pepsin complex, it can certainly be concluded that all of the complexes studied had some activity and that the enzyme complexes had particularly strong activity (the enzymatic activity is of course destroyed completely in most cases). The results also show a clear correlation between the solubility of the complexes, and their therapeutic activity.

By visual observations upon inspection of the treated rat stomachs it was found in all cases that the colours of the stomachs were darker than those of the controls, and that there were substantially darker fringes visible around the ulcers. This is consistent with observations made on human patients treated with pepsin complex preparation, where the preparation was found to result in a heavy coating of bismuth bearing material on the ulcer sites.

What I claim is:

1. A pharmaceutical preparation comprising a therapeutically effective amount of at least one essentially non-dialysable physiologically acceptable complex between:
    (a) bismuth in its trivalent state of oxidation and
    (b) a physiologically acceptable, water-soluble proteinaceous molecule having an affinity for said bismuth,
    (c) ammonia
    (d) a complex-forming organic acid,
said complex being essentially water-soluble to the extent that it forms a sufficient concentration in the water-dissolved state to exhibit anti-ulcer activity in the gastro-intestinal tract, being essentially reversibly precipitable by alcohol and in which the bismuth remains essentially complexed with the proteinaceous matter under the conditions of dialysis, the complex itself being non-dialysable.

2. A preparation according to claim 1 wherein said complex includes ammonia and an organic acid capable of forming watersoluble salts with bismuth.

3. A preparation according to claim 2 wherein said complex additionally includes molecules of physiologically acceptable complex forming sugars, glycols or glycerols and is maintained in aqueous solution of which the pH is adjusted to about 9-10.

4. A preparation according to claim 1 wherein the proteinaceous molecule is a globular protein which has been subjected to mild denaturation and chemical degradation, sufficiently so to open up the globular structure of the globular protein and to produce said affinity whilst essentially preserving the non-dialysable molecular size of the protein.

5. A preparation according to claim 4 which is an addition product of said protein and a watersoluble double salt of bismuth.

6. A preparation according to claim 4 which is an addition product of said protein and a watersoluble physiologically compatable bismuth ammonium salt of an organic hydroxy acid.

7. A preparation according to claim 6 wherein the globular protein is selected from the group consisting of pepsin, trypsin, papain, casein and albumins.

8. A preparation according to claim 7, wherein the globular protein is pepsin.

9. A preparation according to claim 1 in the form of an aqueous solution containing at least 27 mg bismuth per ml of said solution, derived from a water soluble bismuth ammonium salt of an organic hydroxy acid, at least 10 percent of said bismuth being stable against removal by dialysis.

10. A preparation according to claim 4 in the form of an aqueous syrup wherein at least 3 mg/ml of said bismuth is stable against removal by dialysis,
    the complex being an addition product of a substance selected from the group consisting of bismuth ammonium citrate, bismuth ammonium tartrate, bismuth ammonium lactate, and
    bismuth ammonium malate
    and wherein the globular protein is selected from the group consisting of pepsin, papain, and trypsin.

11. A preparation according to claim 4 in the form of a syrup wherein at least 3 mg/ml of said bismuth is stable against removal by dialysis, the complex being an addition product of a water-soluble bismuth ammonium salt of a lower hydroxy carboxylic acid,
    and wherein the globular protein is pepsin.

12. A pharmaceutical preparation according to claim 1 consisting essentially of said at least one essentially non-dialysable physiologically acceptable complex.

13. Process for the manufacture of a pharmaceutical preparation having anti-inflammatory and anti-ulcer efficacy in the gastro-intestinal tract which comprises bringing into intimate contact with one another in an aqueous moderately alkaline medium in a pH range in which they are soluble:
(a) a water-soluble double salt of bismuth in its trivalent state of oxidation, ammonia and an organic acid, and
(b) a physiologically acceptable, water-soluble proteinaceous substances having sites in its molecule capable of accommodating said bismuth as a complex and maintaining said contact at a temperature not exceeding 65° C. until a water-soluble proteinaceous bismuth complex has been formed which is reversibly precipitable by alcohol, bismuth being bound so strongly as to be stable against removal by dialysis, the complex as a whole being non-dialysable, and incorporating said complex in an effective concentration in a pharmaceutical form of presentation adapted for carrying the complex into a region to be treated.

14. Process according to claim 13 carried out in the presence of ammonium ion.

15. Process according to claim 14 wherein the aqueous medium also contains in a dissolved form a lower carboxylic hydroxy acid.

16. Process according to claim 13 wherein the complex is brought into syrup form containing at least 3 mg/ml of bismuth bound in said form which is stable against removal by dialysis.

17. Process according to claim 13 including a step of concentrating the complex to a concentration at which there is present at least 3 mg/ml of bismuth bound in said form which is stable against removal by dialysis.

18. Process according to claim 13 wherein the proteinaceous substance is a globular protein and wherein said contact is maintained for several hours with gentle heating under alkaline conditions until the globular structure of the globular protein has been opened up sufficiently to render the molecule capable of said complex formation with bismuth, whilst essentially preserving the nondialysable molecular size of the protein.

19. Process according to claim 18 wherein said contact is maintained at a pH up to about 10 and a temperature up to about 60° C. and wherein the final pH is adjusted to about 9 to 10.

20. A process as claimed in claim 13 wherein there is present during said contact in said aqueous moderately alkaline medium a sugar, glycerol or glycol.

21. A method of treating a patient suffering from ulceration of the gastro-intestinal tract which comprises introducing to the region of ulceration a pharmaceutical preparation as defined in claim 1 in amounts effective to heal said ulceration.

22. A method according to claim 21 applied to the healing of peptic ulceration.

23. A method of treating a patient suffering from peptic ulceration which comprises administering orally to such patient a pharmaceutical preparation as defined by claim 10 in amounts effective to heal said ulceration.

24. A method according to claim 23 wherein the diet of the patient is adapted to favour gastric acidity.

25. A method of prophylactic therapy for patients treated with drugs having a tendency to cause the formation of peptic ulcers, which comprises administering orally to such patient a pharmaceutical preparation as defined by claim 1 in an amount effective to combat said tendency.

* * * * *